(12) United States Patent
Hojeibane

(10) Patent No.: US 6,258,116 B1
(45) Date of Patent: Jul. 10, 2001

(54) BIFURCATED AXIALLY FLEXIBLE STENT

(75) Inventor: Hikmat Hojeibane, Princeton, NJ (US)

(73) Assignee: Cordis Corporation, Warren, NJ (US)

( * ) Notice: Subject to any disclaimer, the term of this patent is extended or adjusted under 35 U.S.C. 154(b) by 0 days.

(21) Appl. No.: 09/256,914

(22) Filed: Feb. 24, 1999

Related U.S. Application Data

(63) Continuation-in-part of application No. 09/028,383, filed on Feb. 24, 1998, now Pat. No. 6,017,363, which is a continuation-in-part of application No. 08/934,974, filed on Sep. 22, 1997, now Pat. No. 5,938,682.

(60) Provisional application No. 60/010,686, filed on Jan. 26, 1996, now abandoned, provisional application No. 60/017,479, filed on Apr. 26, 1996, now abandoned, provisional application No. 60/017,415, filed on May 8, 1996, provisional application No. 60/024,110, filed on Aug. 16, 1996, and provisional application No. 08/770,236, filed on Dec. 20, 1996, now Pat. No. 5,895,406.

(51) Int. Cl.$^7$ ......................................... A61F 2/06
(52) U.S. Cl. ............................. 623/1.16; 623/1.35
(58) Field of Search .................... 623/1.35, 1.16

(56) References Cited

U.S. PATENT DOCUMENTS

| D. 359,802 | 6/1995 | Fontaine .............. D24/155 |
|---|---|---|
| 3,657,744 | 4/1972 | Ersek . |
| 4,441,216 | 4/1984 | Ionescu et al. ............... 3/1.5 |
| 4,503,569 | 3/1985 | Dotter . |
| 4,553,545 | 11/1985 | Maass et al. . |
| 4,580,568 | 4/1986 | Gianturco ............... 128/345 |
| 4,733,665 | 3/1988 | Palmaz . |
| 4,776,337 | 10/1988 | Palmaz . |

(List continued on next page.)

FOREIGN PATENT DOCUMENTS

| 3205942 A1 | 9/1983 | (DE) | ............. A61M/25/00 |
|---|---|---|---|
| 0 540 290 A2 | 10/1992 | (EP) | ............. A61F/2/06 |
| 0734698 A2 | 3/1996 | (EP) | ............. A61F/2/06 |
| 0800801 A1 | 8/1996 | (EP) | ............. A61F/2/06 |
| 0830853 A1 | 7/1997 | (EP) | ............. A61F/2/06 |
| 0 540 290 A3 | 10/1999 | (EP) | ............. A61F/2/06 |
| 0 566 807 A1 | 4/1992 | (FR) . | |
| 1 205 743 | 9/1970 | (GB) | ............. A61M/29/00 |
| 0 662 307 A2 | 12/1994 | (GB) . | |
| WO96/26689 | 9/1996 | (WO) | ............. A61F/2/06 |
| WO 96/34580 | 11/1996 | (WO) | ............. A61F/2/06 |
| WO97/25000 | 7/1997 | (WO) | ............. A61F/2/04 |
| WO 98/19628 | 5/1998 | (WO) | ............. A61F/2/06 |

\* cited by examiner

*Primary Examiner*—Corrine McDermott
*Assistant Examiner*—Choon P. Koh

(57) ABSTRACT

There is disclosed a method of stent placement which comprises first guiding a guidewire through the vasculature. Second, a balloon catheter which contains two guidewire lumens is strung along the guidewire into position at the bifurcation. The distal opening of the second guidewire lumen abuts the proximal end of the bifurcation. Thereafter, a second guidewire is strung through the first balloon catheter and out the distal opening of the second guidewire lumen. Thus, resident in the second bifurcation leg is the second guidewire. Then, a second standard stent delivery balloon catheter is guided along the second guidewire to a position within the bifurcation. Typically, expansion of both stents can be done one right after the other after proper placement of the first and second balloons.

6 Claims, 18 Drawing Sheets

U.S. PATENT DOCUMENTS

| | | | |
|---|---|---|---|
| 4,800,882 | 1/1989 | Gianturco | 128/343 |
| 4,856,516 | 8/1989 | Hillstead | 128/343 |
| 4,886,062 | 12/1989 | Wiktor | 128/343 |
| 4,907,336 | 3/1990 | Gianturco | 29/515 |
| 4,969,458 | 11/1990 | Wiktor | 606/194 |
| 4,990,131 | 2/1991 | Dardik | 600/36 |
| 4,990,155 | 2/1991 | Wilkoff | 606/191 |
| 4,994,071 | 2/1991 | MacGregor | 606/194 |
| 5,015,253 | 5/1991 | MacGregor | 623/1 |
| 5,035,706 | 7/1991 | Gianturco | 606/198 |
| 5,041,126 | 8/1991 | Gianturco | 606/195 |
| 5,064,435 | 11/1991 | Porter | 623/12 |
| 5,102,417 | 4/1992 | Palmaz . | |
| 5,104,404 | 4/1992 | Wolff | 612/1 |
| 5,116,365 | 5/1992 | Hillstead | 623/1 |
| 5,122,154 | 6/1992 | Rhodes | 606/198 |
| 5,131,908 | 7/1992 | Dardik et al. | 600/36 |
| 5,133,732 | 7/1992 | Wiktor | 606/195 |
| 5,135,536 | 8/1992 | Hillstead | 606/195 |
| 5,163,958 | 11/1992 | Pinchuk | 623/11 |
| 5,171,262 | 12/1992 | MacGregor | 623/1 |
| 5,176,660 | 1/1993 | Truckai | 604/282 |
| 5,178,618 | 1/1993 | Kandarpa | 606/28 |
| 5,192,307 | 3/1993 | Wall | 623/1 |
| 5,195,984 | 3/1993 | Schatz . | |
| 5,217,483 | 6/1993 | Tower | 606/198 |
| 5,222,971 | 6/1993 | Willard et al. | 606/158 |
| 5,246,445 | 9/1993 | Yachia et al. | 606/108 |
| 5,258,021 | 11/1993 | Duran | 623/2 |
| 5,266,073 | 11/1993 | Wall | 623/1 |
| 5,275,622 | 1/1994 | Lazarus et al. | 623/1 |
| 5,282,823 | 2/1994 | Schwartz et al. | 606/198 |
| 5,282,824 | 2/1994 | Gianturco | 606/198 |
| 5,290,305 | 3/1994 | Inoue . | |
| 5,292,331 | 3/1994 | Boneau | 606/198 |
| 5,304,200 | 4/1994 | Spaulding | 606/198 |
| 5,314,444 | 5/1994 | Gianturco | 606/195 |
| 5,314,472 | 5/1994 | Fontaine | 623/12 |
| 5,334,301 | 8/1994 | Heinke et al. | 204/267 |
| 5,342,387 | 8/1994 | Summersq | 606/198 |
| 5,354,257 | 10/1994 | Roubin et al. | 600/7 |
| 5,354,308 | 10/1994 | Simon et al. | 606/198 |
| 5,366,504 | 11/1994 | Andersen et al. | 623/11 |
| 5,370,683 | 12/1994 | Fontaine | 623/1 |
| 5,370,691 | 12/1994 | Samson | 623/12 |
| 5,375,612 | 12/1994 | Cottenceau et al. | 128/899 |
| 5,376,112 | 12/1994 | Duran | 623/2 |
| 5,382,261 | 1/1995 | Palmaz | 606/158 |
| 5,387,235 | 2/1995 | Chuter | 623/1 |
| 5,389,106 | 2/1995 | Tower | 606/198 |
| 5,395,390 | 3/1995 | Simon et al. | 606/198 |
| 5,397,355 | 3/1995 | Marin et al. | 623/12 |
| 5,403,341 | 4/1995 | Solar | 606/198 |
| 5,405,377 | 4/1995 | Cragg | 623/1 |
| 5,411,549 | 5/1995 | Peters | 623/1 |
| 5,421,955 | 6/1995 | Lau et al. . | |
| 5,423,885 | 6/1995 | Williams | 623/1 |
| 5,441,515 | 8/1995 | Khosravi et al. | 606/194 |
| 5,441,516 | 8/1995 | Wang et al. | 606/198 |
| 5,443,477 | 8/1995 | Marin et al. | 606/198 |
| 5,443,496 | 8/1995 | Schwartz et al. | 623/1 |
| 5,443,498 | 8/1995 | Fontaine | 623/1 |
| 5,443,500 | 8/1995 | Sigwart | 623/1 |
| 5,449,372 | 9/1995 | Schmaltz et al. | 606/198 |
| 5,449,373 | 9/1995 | Pinchasik et al. . | |
| 5,449,382 | 9/1995 | Dayton | 623/1 |
| 5,496,365 | 3/1996 | Fontaine et al. . | |
| 5,527,354 | 6/1996 | Fontaine et al. . | |
| 5,569,295 | 10/1996 | Lam . | |
| 5,591,197 | 1/1997 | Orth et al. . | |
| 5,632,763 | 5/1997 | Glastra | 606/194 |
| 5,643,312 | 7/1997 | Fischell et al. | 606/198 |
| 5,649,952 | 7/1997 | Lam . | |
| 5,653,747 | 8/1997 | Dereume | 623/1 |
| 5,669,924 | 9/1997 | Shaknovich | 606/108 |
| 5,697,971 | 12/1997 | Fischell et al. . | |
| 5,723,004 | 3/1998 | Dereume et al. | 623/1 |
| 5,755,734 | 5/1998 | Richter et al. | 606/194 |
| 5,755,771 | 5/1998 | Penn et al. | 623/1 |
| 5,776,161 * | 7/1998 | Globerman | 623/1.35 |
| 5,782,906 | 7/1998 | Marshall et al. | 623/1 |
| 5,800,508 | 9/1998 | Goicoechea et al. | 623/1 |
| 5,861,027 | 1/1999 | Trapp | 623/1 |
| 5,893,887 | 4/1999 | Jayaraman | 623/1 |
| 5,906,640 | 5/1999 | Penn et al. | 623/1 |
| 6,056,775 * | 5/2000 | Borghi et al. | 623/1.16 |

BIFURCATED AXIALLY FLEXIBLE STENT

CROSS REFERENCE

This application is a continuation-in-part of Ser. No. 09/028,383, filed Feb. 24, 1998, Pat. No. 6,017,363 which is a continuation-in-part and claims priority from U.S. application Ser. No. 08/934,974, filed Sep. 22, 1997, Pat. No. 5,938,682. Serial No. 08/934,974 claims priority from U.S. application Ser. No. 60/010,686, filed Jan. 26, 1996, now abandoned; and U.S. application Ser. No. 60/017,479, filed Apr. 26, 1996, now abandoned; and U.S. application Ser. No. 60/017,415 filed May 8, 1996; and U.S. application Ser. No. 60/024,110, filed Aug. 16, 1996; and U.S. application Ser. No. 08/770,236, filed Dec. 20, 1996, Pat. No. 5,895,406 all such patent applications of which are incorporated herein by reference.

FIELD OF THE INVENTION

Generally, this invention relates to balloon catheters. More specifically, this invention relates to balloon catheters used for stent delivery. Most specifically, this invention relates to balloon catheters useful for delivering bifurcated stents. In particular, this invention relates to balloon catheters, which deliver stents to an arterial bifurcation.

BACKGROUND OF THE INVENTION

A stent is commonly used as a tubular structure left inside the lumen of a duct to relieve an obstruction. Commonly, stents are inserted into the lumen in a non expanded form and are then expanded autonomously (or with the aid of a second device in situ. A typical method of expansion occurs through the use of a catheter mounted angioplasty balloon which is inflated within the stenosed vessel or body passageway in order to shear and disrupt the obstructions a associated with the wall components of the vessel and to obtain an enlarged lumen.

In the absence of a sent, restenosis may occur as a result of elastic recoil of the stenotic lesion. Although a number of stent designs have been reported, these designs have suffered from a number of limitations. These include restrictions on the dimension of the scent such as describes a stent which has rigid ends (8 mm) and a flexible median part of 7–21 mm. This device is formed of multiple parts and is not continuously flexible along the longitudinal axis. Other stent designs with rigid segments and flexible segments have also been described.

Other stents are described as longitudinally flexible but consist of a plurality of cylindrical elements connected by flexible members. This design has at least one important disadvantage, for example, according to this design, protruding edges occur when the stent is flexed around a curve raising the possibility of inadvertent retention of the stent on plaque deposited on arterial walls. This may cause the stent to embolize or more out of position and further cause damage to the interior lining of healthy vessels. (See FIG. 1(a) below).

Thus, stents known in the art, which may be expanded by balloon angioplasty, generally compromise axial flexibility to permit expansion and provide overall structural integrity.

Catheter balloons and medical devices incorporating them are well known for use in the surgical arena. For instance, during angioplasty, stenoses and/or obstructions in blood vessels and other body passageways are altered, in order to increase blood flow through the obstructed area of the blood vessel. For example, in a typical balloon angioplasty procedure, a partially occluded lumen is enlarged through the use of a balloon catheter that is passed percutaneously by way of the arterial system by way to the site of the vascular obstruction. The balloon is then deflated to dilate the vessel lumen at the site of the obstruction.

Furthermore, another typical procedure uses a "scaffolding," or stent placed on the balloon angioplasty catheter for similar delivery through the arterial system to the site of a vascular obstruction. Thereafter, the balloon angioplasty catheter is inflated, thereby expanding the stent placed on the catheter. When the stent expands, it similarly expands the lumen so that after removal of the deflated catheter, the stent is retained in its expanded position and thereby holds open that formerly obstructed area of the body passageway.

Essentially, a balloon catheter is a thin, flexible length of tubing having a small inflatable balloon at a desired location along its length such as at or near its tip. Balloon catheters are designed to be inserted into a body passageway such as the lumen of a blood vessel, a passageway in the heart, a urological passageway, and the like. Typically, the passage of the balloon catheter into the body passageway is done with guidance, such as x-ray or fluoroscopic guidance.

In practice, stent delivery is quite complex. That is, a stent is sometimes required to be placed in a rather tortuous area of the vasculature. In this instance, it is often necessary to have a catheter which is capable of negotiating tight turns, and/or being placed along a bifurcated length of blood vessel. In some instances, while a generally occluded section of blood vessel can readily be stented, it is often difficult to place a second stent at the other portion of a bifurcation. In other words, one can imagine the bifurcation as an inverted letter "Y" within the body. (The approach of the catheter concerning this inverted "Y" shape is generally through one of the legs in the "Y".) Therefore, the balloon passes both between the leg and the trunk or base of the "Y" rather readily. However, once a stent is placed along these two legs, it is rather difficult to place a second stent at or near the junction of the first leg and the base of the letter "Y". Of course, the same can hold true when the approach is via the base of the "Y" and delivery of the first stent is to one of the legs. This is all the more true because as one advances through the vasculature, the arterial sizes go from quite large (greater than 1 cm diameter) to rather small (some time less than 2.5 mm diameter).

It would be desirable, therefore, to create a system which allows for delivery of a single stent or pair of stents at a bifurcation in the vasculature. It would further be desirable for this stent or for this delivery system to be able to negotiate the bends of the bifurcation, and moreover, to provide for easy access when one stent is already placed. Furthermore, it would be quite useful in order to be able to apply the second stent, for the first stent to be reliably placed every time so that the user knows exactly where the bifurcation is located, and as well where the stent must be appropriately oriented in order to readily access the second leg of the "Y" of the bifurcation.

Finally, it would be useful for a device such as a desired delivery system to carry a stent capable of allowing secondary access to a bifurcated portion of the vasculature. Thus, it would be most desirable for the device to comprise a catheter capable of balloon delivery of a stent at a bifurcation, and also balloon delivery of a second stent at the bifurcation.

SUMMARY OF THE INVENTION

The present invention overcomes some perceived shortcomings of prior art stents by providing a stent with axial flexibility. In a preferred embodiment, the stent has a first end and a second end with an intermediate section between the two ends. The stent further has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. The wave associated with each of the bands has approximately the same fundamental spatial frequency in the intermediate section, and the bands are so disposed that the waves associated with them are spatially aligned so as to be generally in phase with one another. The spatially aligned bands are connected, at a plurality of periodic locations, by a short circumferential link to an adjacent band.

In particular, at each one of a first group of common axial positions, there is a circumferential link between each of a first set of adjacent pairs of bands.

At each one of a second group of common axial positions, there is a circumferential link between each of a second set of adjacent rows of bands, wherein, along the longitudinal axis, a common axial position occurs alternately in the first group and in the second group, and the first and second sets are selected so that a given band is linked to a neighboring band at only one of the first and second groups of common axial positions.

In a preferred embodiment of the invention, the spatial frequency of the wave associated with each of the bands is decreased in a first end region lying proximate to the first end and in a second end region lying proximate to the second end, in comparison to the spatial frequency of the wave in the intermediate section. In a further embodiment of the invention, the spatial frequency of the bands in the first and second end regions is decreased by 20% compared with the spatial frequency of the bands in the intermediate section. The first end region may be located between the first end and a set of circumferential links lying closest to the first end and the second end region lies between the second end and a set of circumferential links lying closest to the second end. The widths of corresponding sections of the bands in these end regions, measured in a circumferential direction, are greater in the first and second end regions than in the intermediate section. Each band includes a terminus at each of the first and second ends and the adjacent pairs of bands are joined at their termini to form a closed loop.

In a further embodiment of the invention, a stent is provided that has first and second ends with an intermediate section therebetween, the stent further having a longitudinal axis and providing axial flexibility. This stent includes a plurality of longitudinally disposed bands, wherein each band defines a generally continuous wave having a spatial frequency along a line segment parallel to the longitudinal axis, the spatial frequency of the wave associated with each of the bands being decreased in a first end region lying proximate to the first end and in a second end region lying proximate to the second end, in comparison to the spatial frequency of the wave in the intermediate section; and a plurality of links for maintaining the bands in a tubular structure. The first and second regions have been further defined as the region that lies between the first and second ends and a set of circumferential links lying closest to the first end and second end.

In a further embodiment the widths of the sectionals of the bands, measured in a circumferential direction, are greater in the first and second end regions than in the intermediate section.

In yet an additional embodiment, the stent is divided into a group of segments, and each of the segments are connected by a flexible connector. In addition, the stent segments are provided with enhanced flexibility at the flexible connectors, due to the geometrical configuration of the flexible connectors.

Furthermore, the current stent can be modified to provide for bifurcated access, whereas the stent itself is uniform throughout. If the manufacturer designs such a stent to have an essential opening, then it is possible to place the stent such that a pair of stents can be placed one through the other. In this fashion, the stents are capable of being placed at a bifurcation, without any welding or any special attachments. The interlocking mechanism can be incorporated into the stent design to cause the stent to interlock at the desired position during assembly of the device.

In practice, therefore, the current catheter device consists of a balloon catheter which comprises a shaft portion having a proximal and a distal end. The shaft portion has a guidewire lumen therethrough. The lumen has a proximal opening and a distal opening. The distal opening of the shaft portion is located at the distal end of the shaft. A balloon is connected to the shaft at the shaft distal end. The balloon has proximal and distal ends and a first guidewire lumen through it. The balloon guidewire is in fluid communication with the guidewire lumen of the shaft and the first balloon guidewire lumen also has proximal and distal ends. The balloon has a second guidewire lumen, the second guidewire lumen containing a distal opening located proximal to the distal opening of the first guidewire lumen.

Further, there is disclosed a method of stent placement which comprises first guiding a guidewire through the vasculature. Second, a balloon catheter which contains two guidewire lumens is strung along the guidewire into position at the bifurcation. The distal opening of the second guidewire lumen abuts the proximal end of the bifurcation. Thereafter, a second guidewire is strung through the first balloon catheter and out the distal opening of the second guidewire lumen. Thus, resident in the second bifurcation leg is the second guidewire. Then, a second standard stent delivery balloon catheter is guided along the second guidewire to a position within the bifurcation. Typically, expansion of both stents can be done one right after the other after proper placement of the first and second balloons.

BRIEF DESCRIPTION OF THE DRAWINGS

The foregoing aspects of the invention will be more readily understood by reference to the following detailed description, taken with the accompanying drawings, in which.

DETAILED DESCRIPTION OF SPECIFIC EMBODIMENTS

Improvements afforded by embodiments of the present invention include (a) increased flexibility in two planes of the non-expanded stent while maintaining radial strength and a high percentage open area after expansion; (b) even pressure on the expanding stent that ensures the consistent and continuous contact of expanded stent against artery wall; (c) avoidance of protruding parts during bending; (d) removal of existing restrictions on maximum of stent; and reduction of any shortening effect during expansion of the stent.

In a preferred embodiment of the invention, an expandable cylindrical stent 10 is provided having a fenestrated structure for placement in a blood vessel, duct or lumen to hold the vessel, duct or lumen open, more particularly for protecting a segment of artery from restenosis after angioplasty. The stent 10 may be expanded circumferentially and maintained in an expanded configuration, that is circumferentially rigid. The stent 10 is axially flexible and when flexed at a band, the stent 10 avoids any externally protruding component parts.

FIG. 1 shows what happens to a stent 10, of a similar design to a preferred embodiment herein but utilizing instead a series of circumferentially disposed bands, when caused to bend in a manner that is likely encountered within a lumen of the body. A stent 10 with a circumferential arrangement of bands (1) experiences an effect analogous to a series of railroad cars on a track. As the row of railroad cars proceeds around the bend, the corner of each car proceeding around the bend after the coupling is caused to protrude from the contour of the track. Similarly, the serpentine circumferential bands have protrusions (2) above the surface of the stent 10 as the stent 10 bends.

Figure 1A:
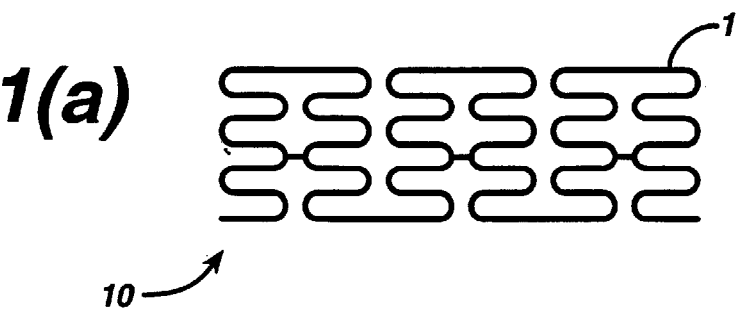
FIGS. 1(a) and 1(b) are side views of a stent having circumferentially disposed bands wherein the stent is in axially unbent and bent positions respectively, the latter showing protruding edges.
Figure 1B:
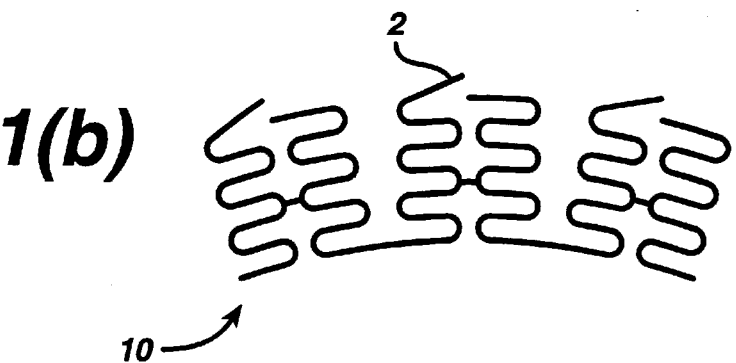
Figure 1C:
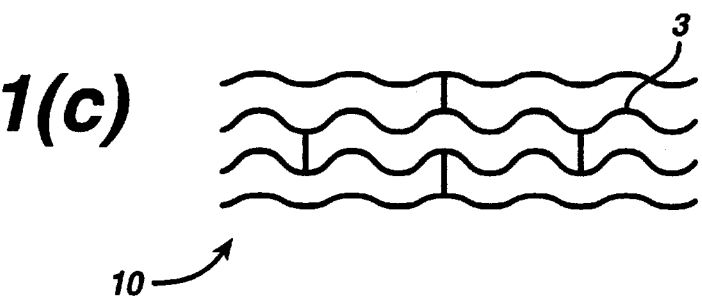
FIGS. 1(c) and 1(d) are side views of an axially flexible stent in accordance with the present invention wherein the stent is in unbent and bent positions respectively, the latter displaying an absence of protruding edges.
Figure 1D:
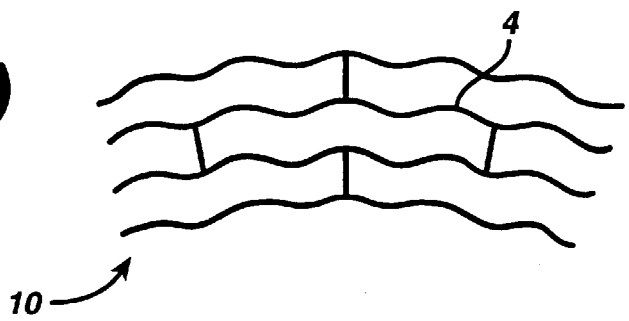
Figure 7:
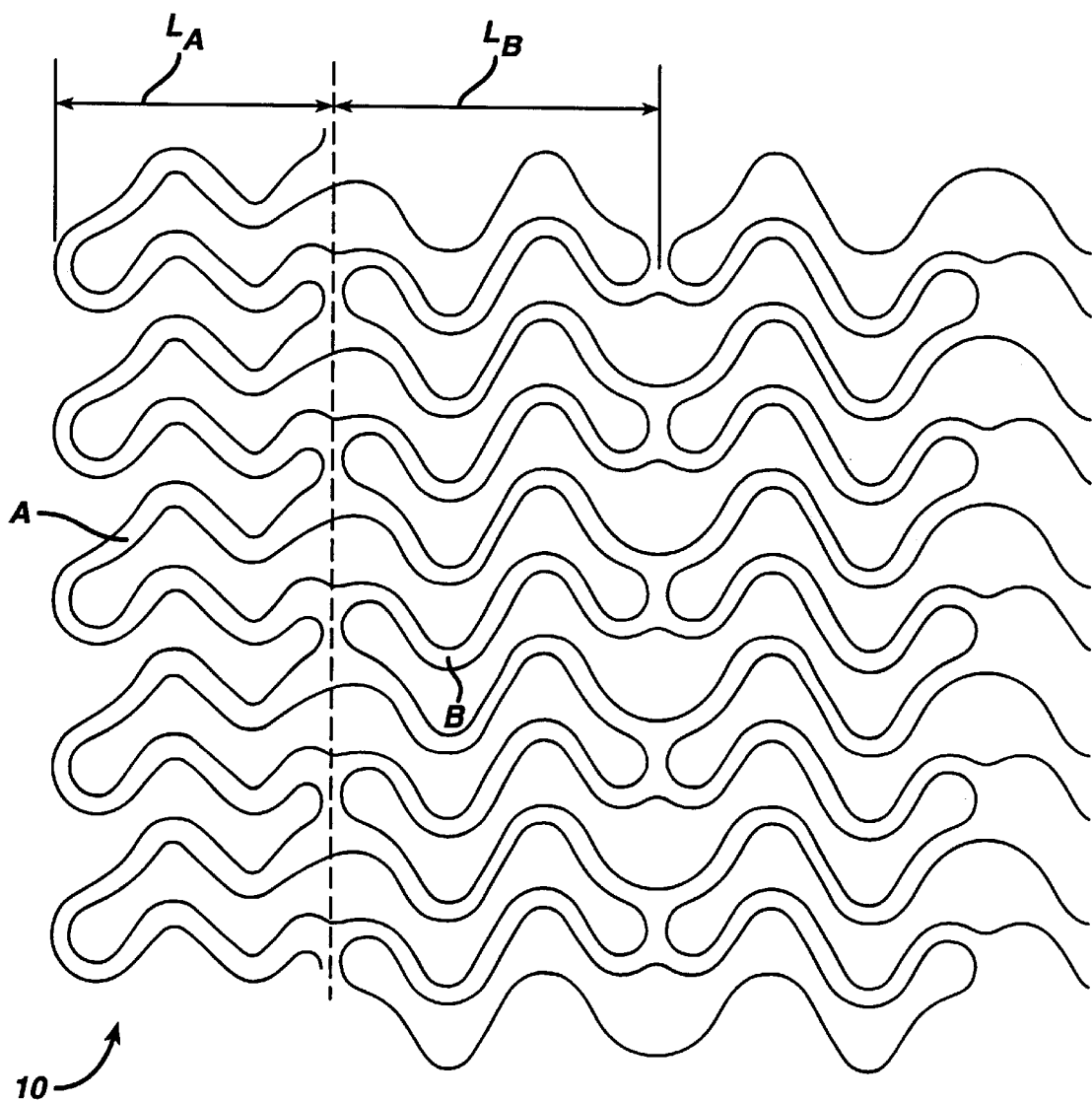
FIG. 7 shows a two dimensional layout of the stent. The ends are modified such that the length ($L_A$) is about 20% shorter than length ($L_B$) and the width of the band A is greater than the width of band B.

The embodiment shown in FIGS. 1(c) and 1(d) and FIG. 7 has bands (3) which are axially flexible and are arranged along the longitudinal axis. This allows the stent to bend so that the bent bands (4) do not protrude from the profile of the curve of the stent 10. Furthermore, any flaring at the ends of the stent 10 that might occur with a stent 10 having a uniform structure is substantially eliminated by introducing a modification at the ends of the stent 10. This modification comprises decreasing the spatial frequency and increasing the width of the corresponding bands in a circumferential direction ($L_A$ and A) compared to that of the intermediate section. ($l_B$ and B).

In an embodiment of the invention, the spatial frequency $L_A$ may be decreased 0–50% with respect to $L_B$, and the width A may be increased in the range of 0–150% with respect to B. Other modifications at the ends of the stent 10 may include increasing the thickness of the wall of the stent 10 and selective electropolishing. These modifications protect the artery and any plaque from abrasion that may be caused by the stent 10 ends during insertion of the stent 10. The modification also may provide increased radio-opacity at the ends of the stent 10. Hence it may be possible to more accurately locate the stent 10 once it is in place in the body.

Figure 2:
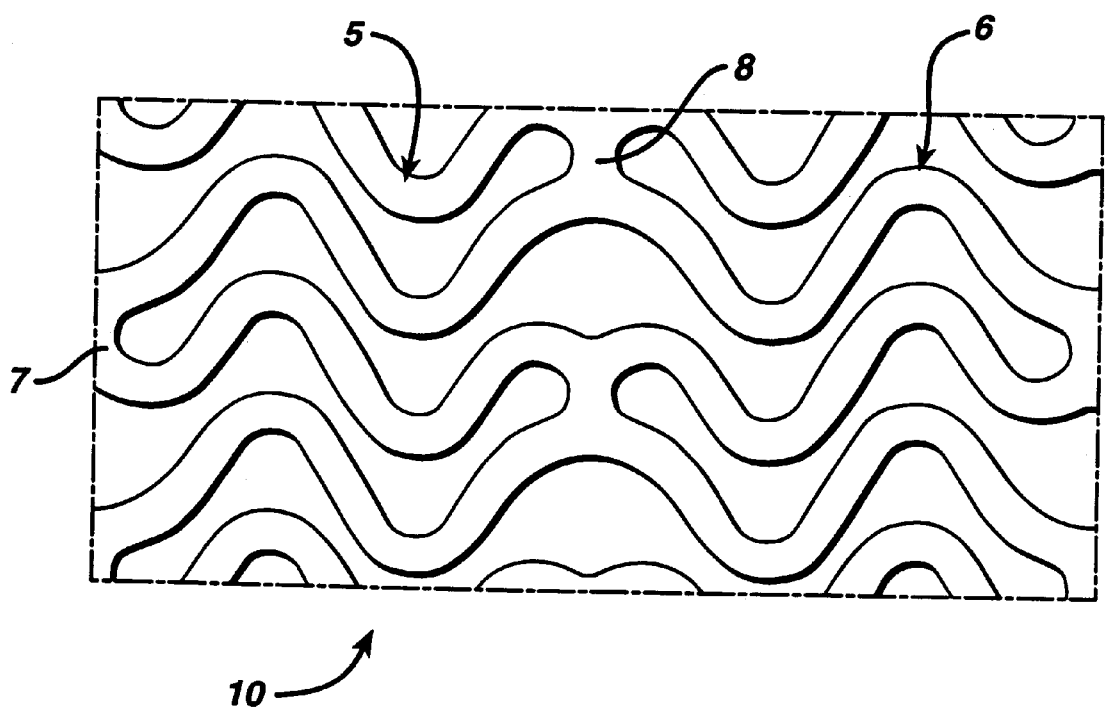
FIG. 2 is a side view of a portion of the stent of FIGS. 1(c) and 1(d) showing the longitudinal bands, spaces, and inner radial measurements of bends in the bands being measured in inches.
Figure 6:
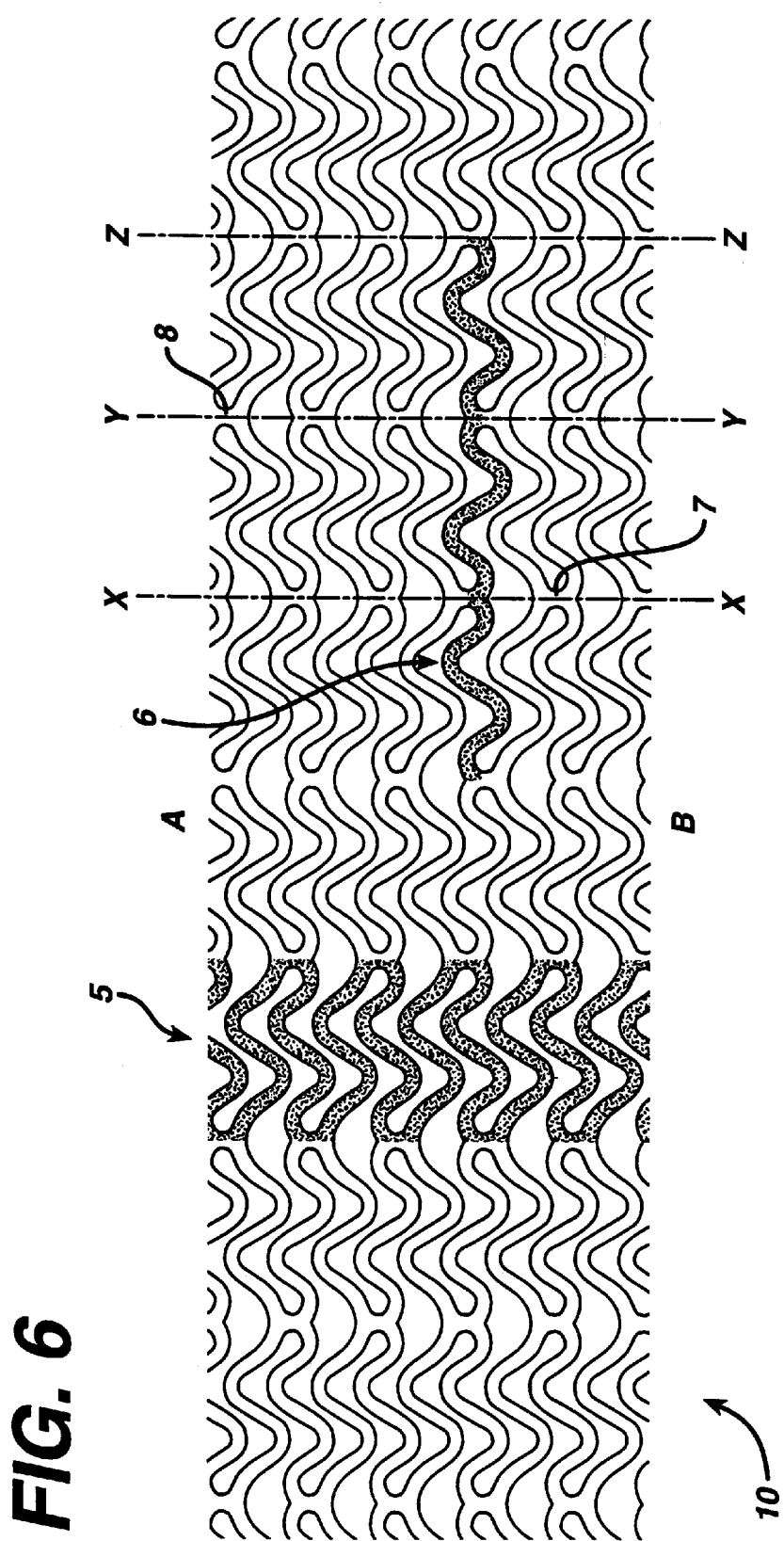
FIG. 6 shows a two-dimensional layout of the stent of FIG. 4 to form a cylinder such that edge "A" meets edge "B", and illustrating the spring-like action provided in circumferential and longitudinal directions.

The embodiment as shown in FIGS. 2 and 6 has the unique advantage of possessing effective "springs" in both circumferential and longitudinal directions shown as items (5) and (6) respectively. These springs provide the stent 10 with the flexibility necessary both to navigate vessels in the body with reduced friction and to expand at the selected site in a manner that provides the final necessary expanded dimensions without undue force while retaining structural resilience of the expanded structure.

Figure 4:
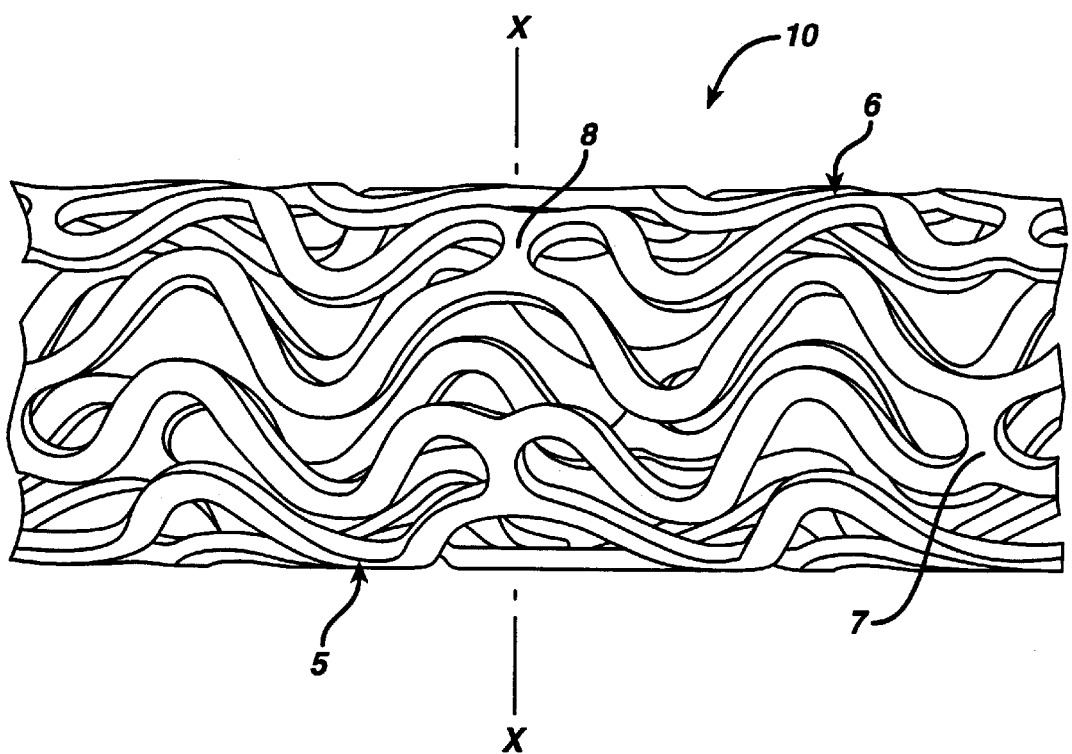
FIG. 4 is a view along the length of a piece of cylindrical stent (ends not shown) prior to expansion showing the exterior surface of the cylinder of the stent and the characteristic banding pattern.
Figure 5:
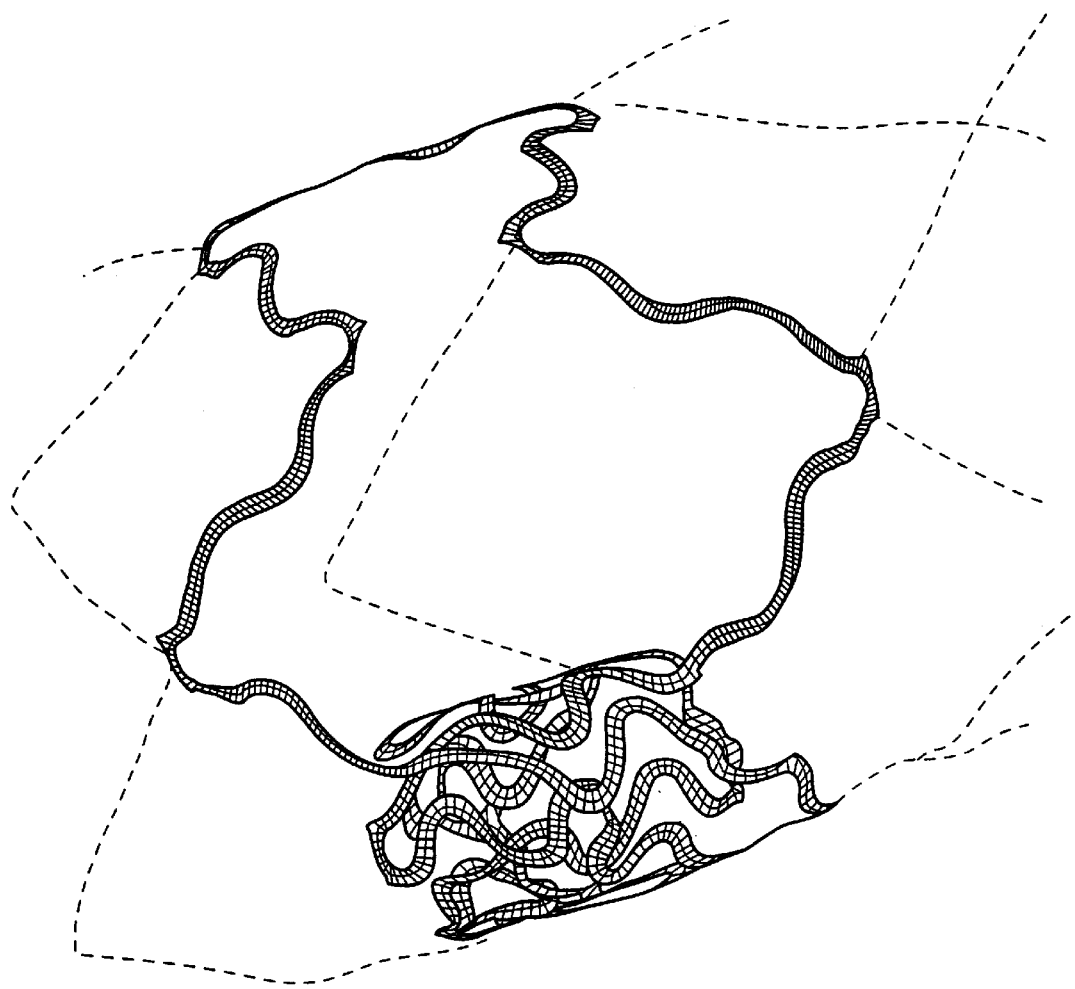
FIG. 5 is an isometric view of a deflection plot where the stent of FIG. 2 is expanded to a larger diameter of 5 mm.

As shown in both FIGS. 2, 4 and 6, each longitudinal band undulates through approximately two cycles before there is formed a circumferential link to an adjacent band. Prior to expansion, the wave W associated with each of the bands may have approximately the same fundamental spatial frequency, and the bands are so disposed that the wave W associated with them are spatially aligned, so as to be generally in phase with one another as shown in FIG. 6.

The aligned bands on the longitudinal axis are connected at a plurality of periodic locations, by a short circumferential link to an adjacent band. Consider a first common axial position such as shown by the line X—X in FIGS. 4 and 6. Here an adjacent pair of bands is joined by circumferential link 7. Similarly other pairs of bands are also linked at this common axial position. At a second common axial position, shown in FIG. 6 by the line Y—Y, an adjacent pair of bands is joined by circumferential link 8. However, any given pair of bands that is linked at X—X is not linked at Y—Y and vice-versa. The X—X pattern of linkages repeats at the common axial position Z—Z. In general, there are thus two groups of common axial positions. In each of the axial positions of any one group are links between the same pairs of adjacent bands, and the groups alternate along the longitudinal axis of the embodiment. In this way, circumferential spring 6 and the longitudinal spring 6 are provided.

A feature of the expansion event is that the pattern of open space in the stent 10 of the embodiment of FIG. 2 before expansion is different from the pattern of the stent 10 after expansion. In particular, in a preferred embodiment, the pattern of open space on the stent 10 before expansion is serpentine, whereas after expansion, the pattern approaches a diamond shape (3a, 3b). In embodiments of the invention, expansion may be achieved using pressure from an expanding balloon or by other mechanical means.

Figure 3A:
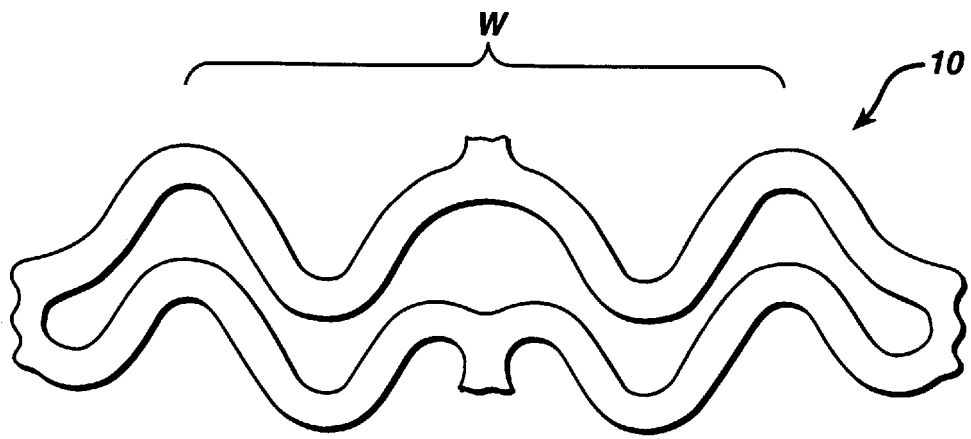
FIGS. 3(a) and 3(b) show a portion of the stent of FIG. 2 with two bands between two circumferential links (a) before expansion in the unexpanded state; and (b) after expansion, in the deformed state.
Figure 3B:
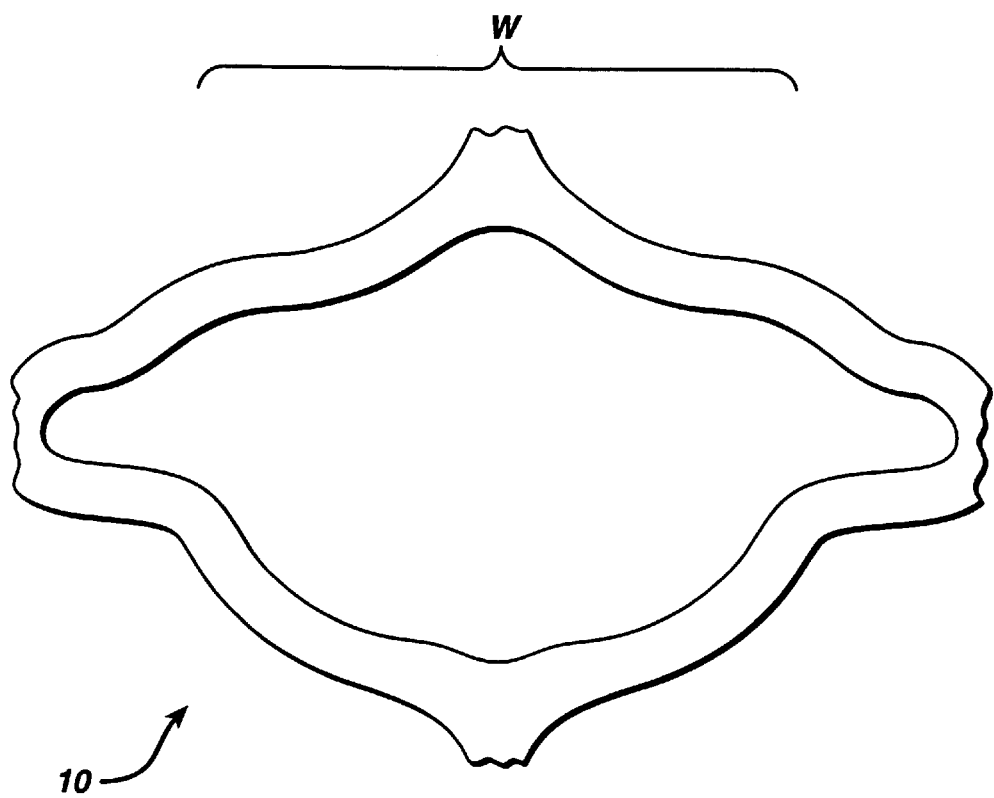

In the course of expansion, as shown in FIG. 3, the wave W shaped bands tend to become straighter. When the bands become straighter, they become stiffer and thereby withstand relatively high radial forces. FIG. 3 shows how radial expansion of the stent 10 causes the fenestrations to open up into a diamond shape with maximum stress being expended on the apices of the diamond along the longitudinal axis. When finite element analyses including strain studies were performed on the stent 10, it was found that maximum strain was experienced on the bands and links and was below the maximum identified as necessary to maintain structural integrity.

The optimization of strain of the stent 10 is achieved by creating as large a turn radius as possible in the wave W associated with each band in the non-expanded stent 10. This is accomplished while preserving a sufficient number of bands and links to preserve the structural integrity of the stent 10 after expansion. In an embodiment of the invention, the strain may be less than 0.57 inches/inch for 316 L stainless steel. The expansion pressure may be 1.0–7.0 atmospheres. The number of bands and the spatial frequency of the wave W on the longitudinal axis also affect the number of circumferential links. The circumferential links contribute structural integrity during application of radial force used in expansion of the stent 10 and in the maintenance of the expanded form. While not being limited to a single set of parameters, examples of a stent 10 of the invention having a longitudinal axis and providing axial flexibility of the type shown in FIG. 6, may include the following: stents 10 having an expanded diameter of 4 mm and a length of 30 mm that for example may have about 8–12 rows, more particularly 10 rows; about 6–10 slots, more particularly 8 slots (a slot is shown in FIG. 6 as extending between X and Z); and a wave W amplitude of about ¼–⅒ of a slot length, more particularly ⅛ of a slot length.

The stents described may be fabricated from many methods. For example, the stents may be fabricated from a hollow or formed stainless steel tube that may be cut out using lasers, electric discharge milling (EDM), chemical etching or other means. The stents are inserted into the body and placed at the desired site in an unexpanded form. In a preferred embodiment, expansion of the stent is effected in a blood vessel by means of a balloon catheter, where the final diameter of the stent is a function of the diameter of the balloon catheter used.

In contrast to stents of the prior art, the stent of the invention can be made at any desired length, most preferably at a nominal 30 mm length that can be extended or diminished by increments, for example 1.9 mm increments.

It will be appreciated that a stent in accordance with the present invention may be embodied in a shape memory material, including, for example, an appropriate alloy of nickel and titanium; or stainless steel. In this embodiment after the stent has been formed, it may be compressed so as to occupy a space sufficiently small as to permit its insertion in a blood vessel or other tissue by insertion means, wherein the insertion means include a suitable catheter, or flexible rod. On emerging from the catheter, the stent may be configured to expand into the desired configuration where the expansion is automatic or triggered by a change in pressure, temperature or electrical stimulation.

An embodiment of the improved stent has utility not only within blood vessels as described above but also in any tubular system of the body such as the bile ducts, the urinary system, the digestive tube, and the tubes of the reproductive system in both men and women.

In yet a further embodiment, there is described a stent 10 as presently disclosed containing a multiplicity of curvilinear segments 20. These curvilinear segments 20 are connected to each other via a generally perpendicular connector 25. The generally perpendicular connector 25 lies substantially in the plane perpendicular to the longitudinal axis of the stent 10. Each of the stent 10 segments as described herein is connected to an adjacent stent 10 segment. This is done using a series of flexible connectors. Importantly, the connectors themselves can be made narrower at their midpoints. This enhances the possibility of flexure at that point. Of course, it is to be realized that alternate designs of the connector to insure flexibility are possible, and contemplated by this invention.

Figure 8:
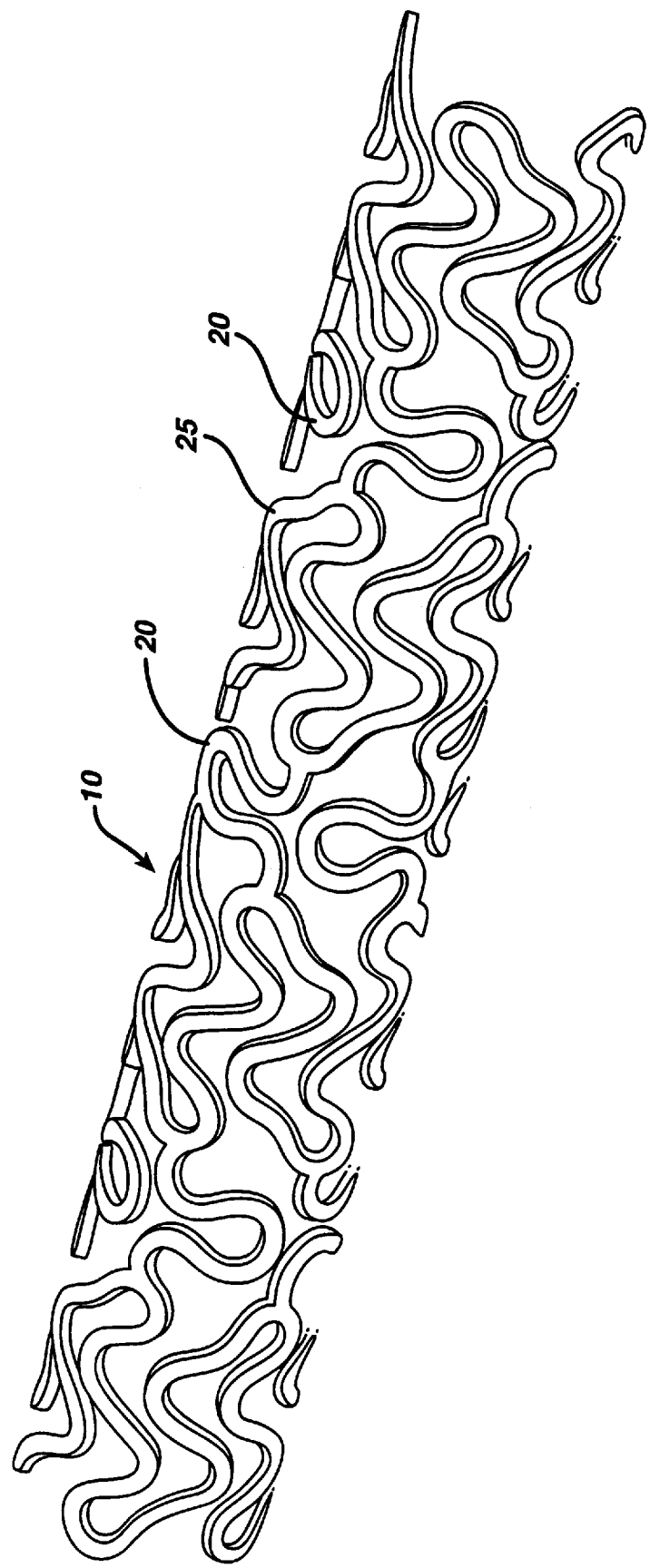
FIG. 8 shows a perspective view of a stent containing flexible connectors as described in the present invention.
Figure 9:
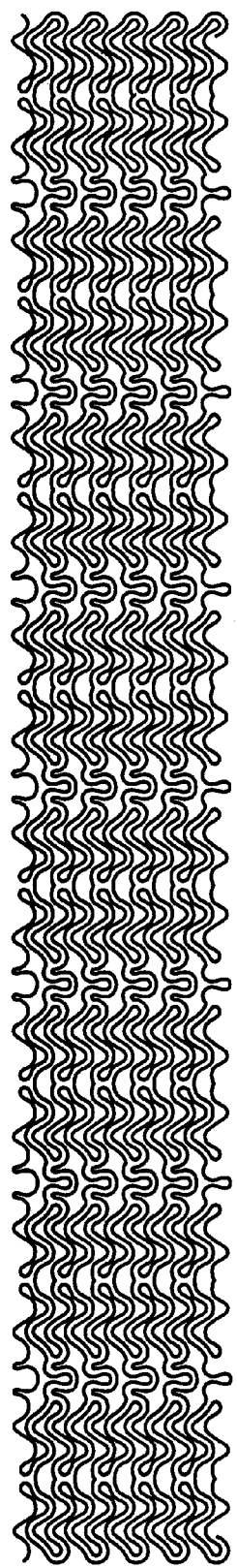
FIG. 9 shows a stent in which the flexible connectors are attached to stent segments, in layout form. These flexible connectors are attached in an every-other-segment pattern.
Figure 10:
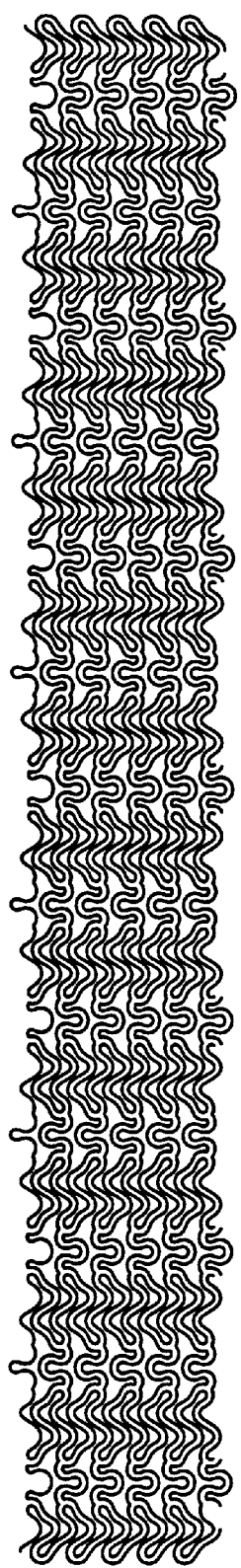
FIG. 10 shows a layout view where the stent segments are connected with a flexible connector in every stent segment pattern.
Figure 11:
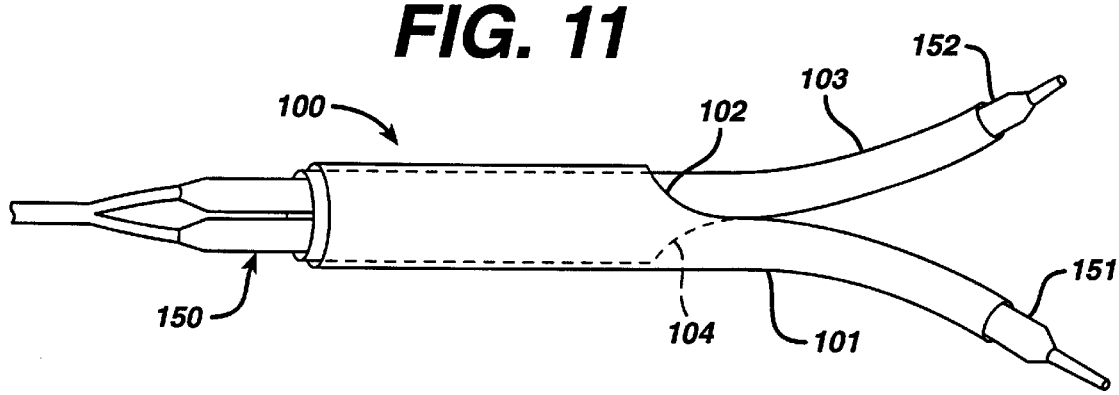
FIG. 11 shows a schematic of the unexpanded stents when loaded on the stent delivery system.
Figure 12:
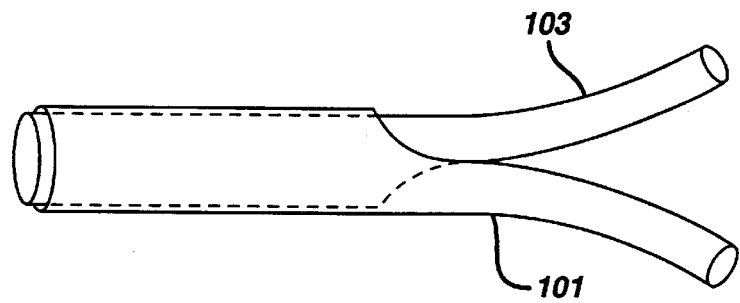
FIG. 12 shows the stents placed alone.

In essence therefore, the stent 10 as described in FIG. 8 is a stent 10 of considerable flexibility when compared to more rigid rectilinear stents. Nonetheless, the stent 10 of the present invention does not depart from the basic concepts set forth herein, in that it discloses a continuously curvilinear strut. This curvilinear strut is connected to other curvilinear struts via a series of "second" more flexible connectors, described above.

In any regard, it can be seen that the stent 10 of the present invention incorporates various new and useful members. One of them is the flexible connector in conjunction with a generally curvilinear stent. Another is the use of the generally larger struts at the ends of the stent 10 in order to provide for continued support at the stent 10 ends. A final aspect is the use of flexible connectors amongst stent 10 segments to provide for greater flexibility.

In all regards, however, it is to be seen that the present invention is to be determined from the attached claims and their equivalents.

As can be seen from FIGS. 11 through 14, an improved device 100 of the present invention can also be made to perform in a bifurcated fashion. In this way, the stent 101 contains a central opening 102. This central opening 102 allows for the passage of an unexpanded stent 103 of the same size. Typically of course, the two stents 101,103 will have the same general configuration, and one can pass through the other on the same type of diameter balloon. In fact, the balloon 150 as seen in the current FIGS. 11–16 is a bifurcated balloon, but need not be. Two separate balloons are certainly capable of performing the same function. The balloons are preferably less than 6 Fr in their unexpanded shape in a preferred embodiment, but of course, need not be so constrained.

As seen in FIGS. 11–14, the first stent 101 (the lower one in the figure) is loaded on one of the balloons 151. It has an opening 102 central to it. This opening faces the upper stent 103 and balloon 152, the upper stent 102 loaded on the second balloon 152. The upper stent 103, when loaded on the second balloon 152 also has an opening 104 which faces the lower stent 101. In this fashion, as the second stent 103 is strung through the first stent 101, it is placed in such a fashion so as to have a mutually facing contact with the first stent 101. Then, as the balloon and stent combination is guided through the human anatomy, the devices will go toward a bifurcation. When this happens, the device is caused to split using various guide wire techniques. Then, each of the respective balloons is inflated.

Figure 13:
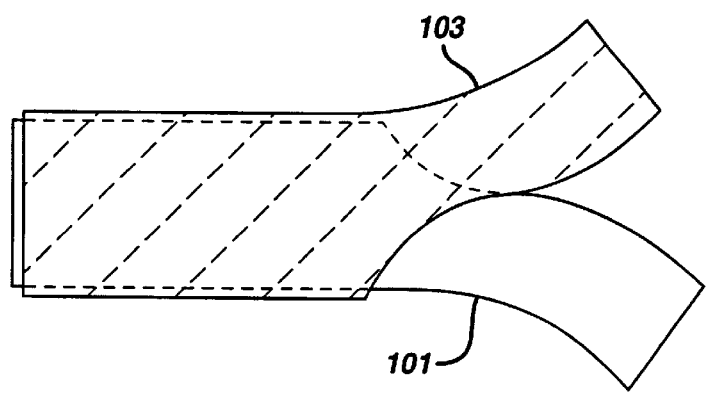
FIG. 13 shows the stents as expanded without the delivery system.
Figure 14:
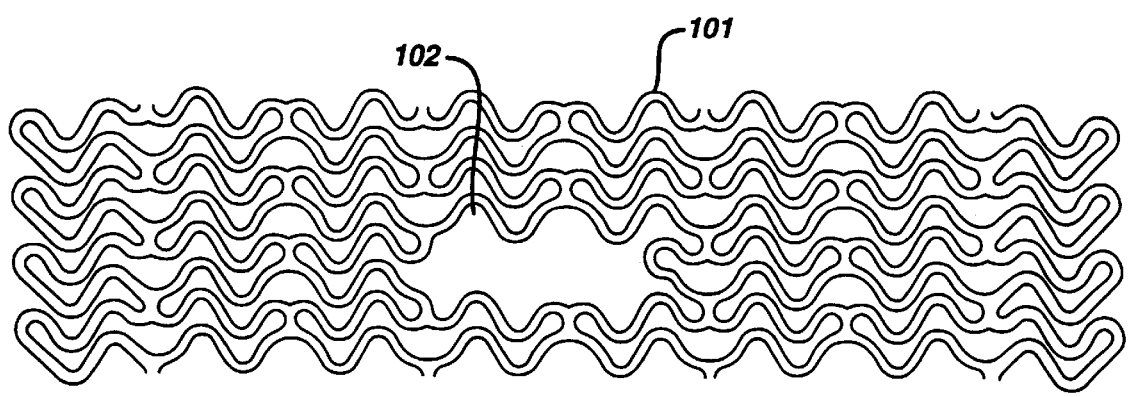
FIG. 14 shows a modification of the stent in a layout view.

On this inflation, the entire device is expanded such as seen in FIG. 13. Thus, the entire bifurcation is covered, and yet in a much easier than typical bifurcated expansions. What is unique is that there is no welding of the stents 101, 103 together, they can be common "off-the-shelf" stents modified only slightly so as to be useful for this particular need.

It should be noted that the stent of FIGS. 11–14 can be designed with any slot or wire configurations or of any high density materials or composites and can be balloon expandable or self-expanding or even the combination of both. The devices can be sold separately from separate catheters to be assembled during the desired procedure by the clinicians; can be used with a bifurcated balloon or two separate balloons; or incorporated with one or more radio-opaque markers to allow for better positioning in radio-opacity. The bifurcated stent delivery system is placed by crimping over two balloons and then expanded at the sight of the lesion.

Figure 15:
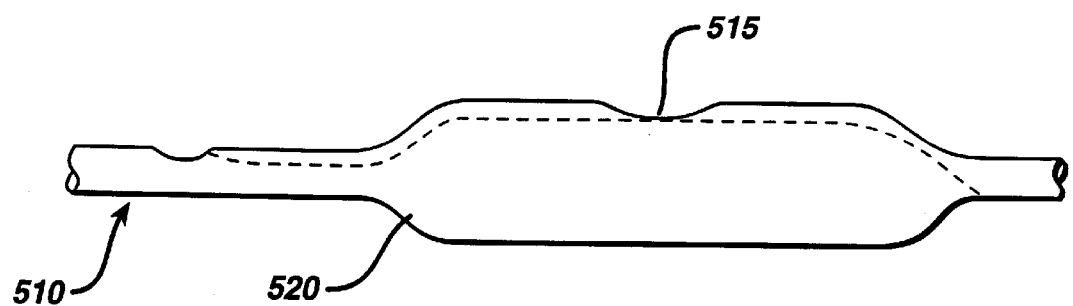
FIG. 15 is a plan view of the balloon of the present system.
Figure 16:
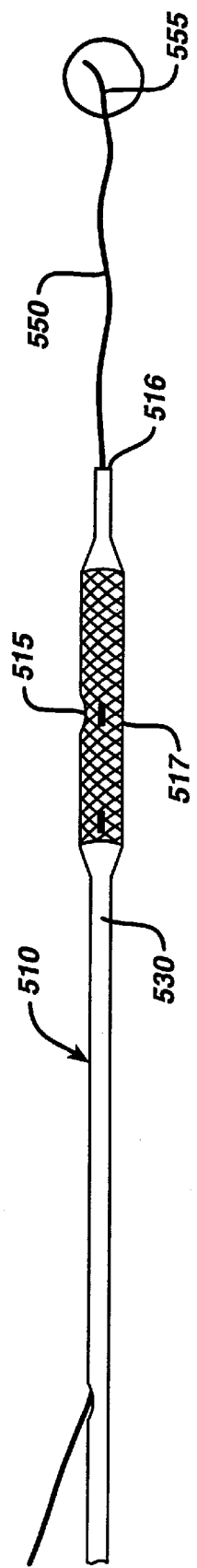
FIG. 16 is an assembly view of the same balloon.
Figure 17:
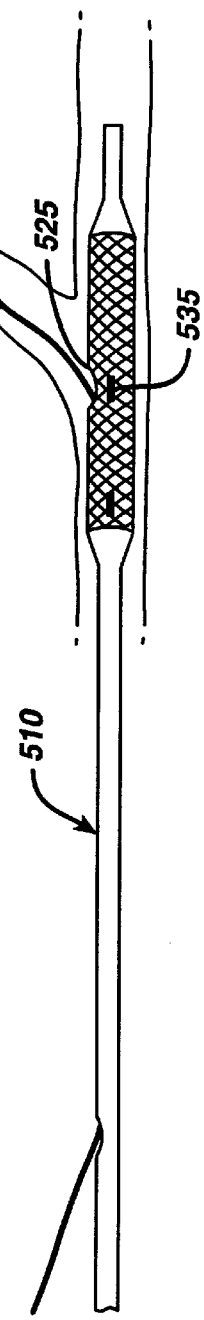
FIG. 17 is a view of the balloon when in use.

As seen from FIGS. 15–17, there is described in this present invention a balloon 510, in which is contained a standard balloon catheter 520. These catheters are described in, for instance, U.S. Pat. Nos. 5,108,415; 5,156,612 and 5,304,197. Such patents are owned by a common assignee of the present invention, and incorporated herein by reference. Uniquely, however, the current balloon 510 contains a side hole 515 in the balloon. The side hole 515 is placed at an exit port 516 in the middle 517 of the balloon 510. This side hole 515 creates access to a lumen 525 created in the side of the catheter 510. Thus, this side hole 515 creates an access channel useful for the stent 101 of the current invention.

So in use therefore, the catheter 510 is advanced into the lumen of the artery, as would be typical angioplasty catheter. First, a guidewire 550 is placed within lumen 530 of the catheter 510. Second, the catheter 510 is tracked over the guidewire and into the lumen. Then, the guidewire 550, specially formed for this use is retracted until its tip 555 is placed at the distal marker 535 of the current catheter 516. Then, the guidewire 550 is rotated so that its tip 555 "pops" out of the side hole 515 created in the side lumen 525 of the present catheter 510. The guidewire 550 is then advanced through the side branch artery to give access to the side branch.

Figure 18:
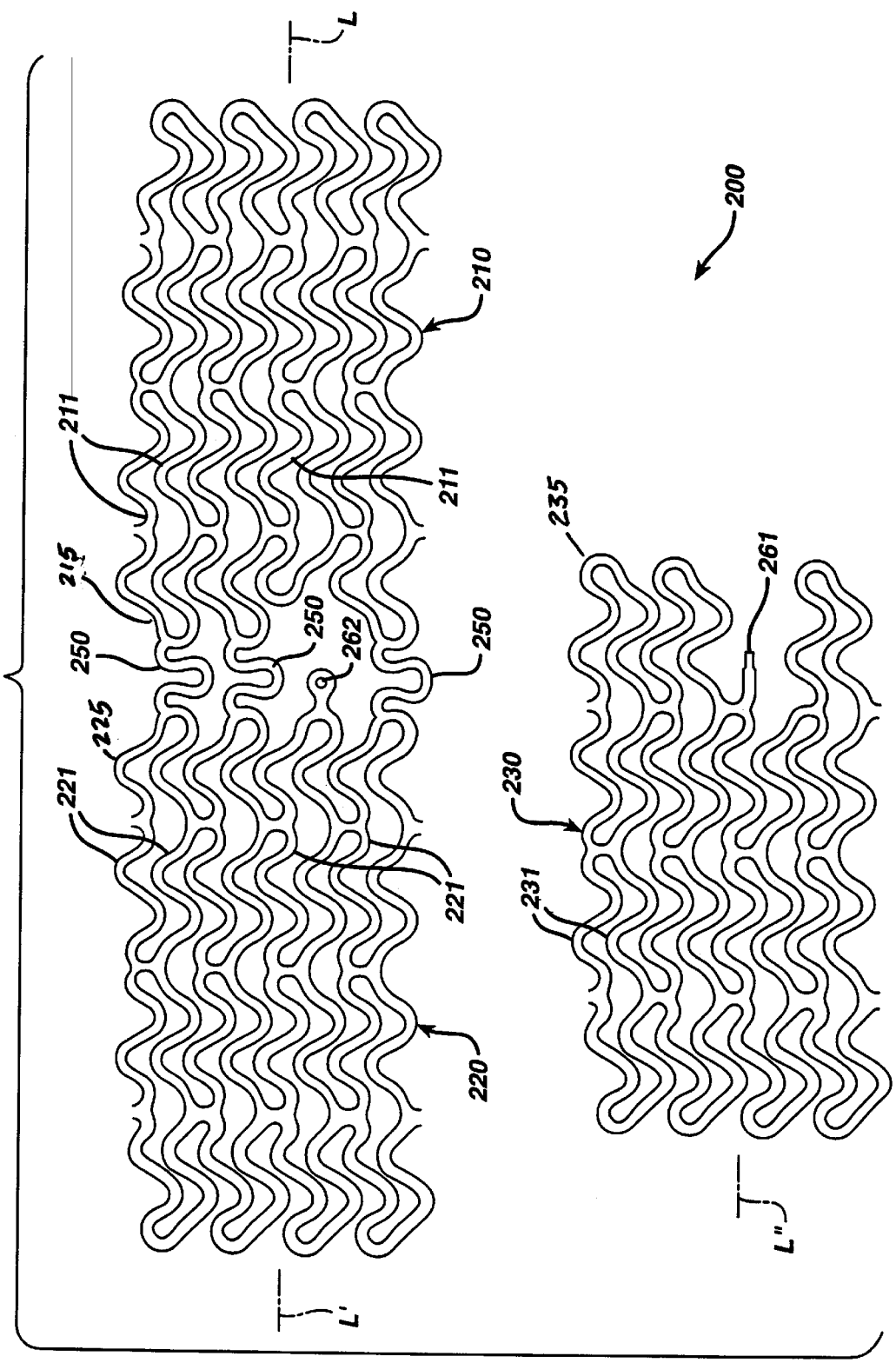
FIG. 18 is a assembly view of another stent which may be used on the balloons of FIGS. 15–17.
Figure 19:
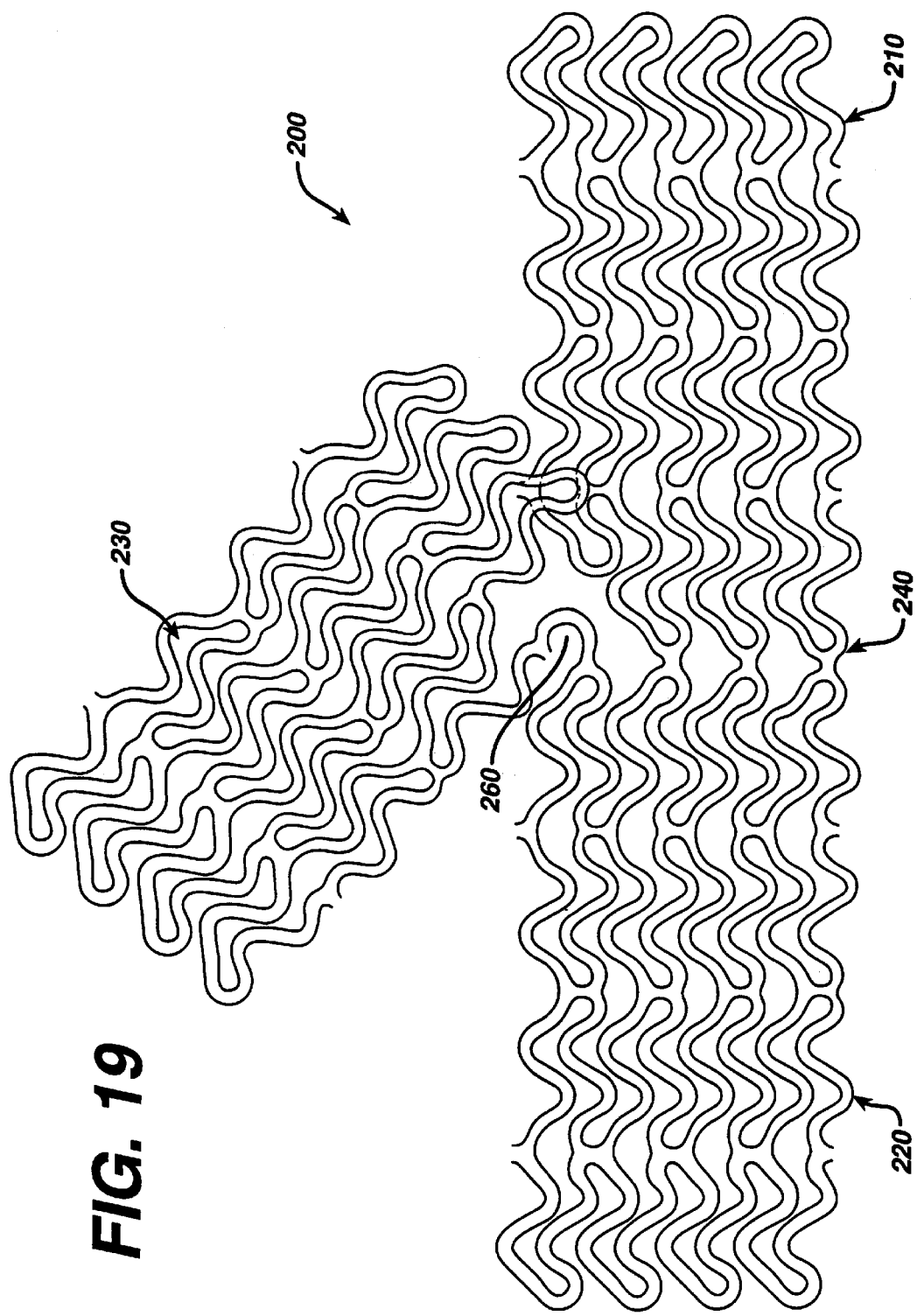
FIG. 19 is a plan view of the stent of the previous figure.

In FIGS. 18–19, the first item described will be the structure of stent 200 in accordance with the invention and illustrated in FIGS. 18–19. The stent 200 is an improvement over other bifurcated stent ideas, in that the stent is continuous through the mid-section 250 of the main branch segment 210, 220. Segment 230 is connected by a weld or other means (such as a pivotable hook or a ball in socket joint) to another section 220 to form the "Y"-shaped stent. Such design will allow for greater vessel coverage at the intersection point of the bifurcation.

As was mentioned earlier, stent 200 comprises three tubular sections (210, 220, and 230) and a continuous connection (240). Sections 210, 220, 230 have struts 211, 221, 231 of sinusoidal shape. Of course, any known shape (e.g., straight struts, are possible).

The first section (210) is a proximal section having as its center axis L. It is intended for insertion into main stem of blood vessel for treatment upstream of a bifurcation.

The first distal section (220) having as its section axis L' is at least approximately aligned with proximal section 210 prior to use. This first distal section 220 is intended for insertion to a blood distal branching off from the bifurcation from a proximal blood vessel, into which section 210 is to be placed. The first distal section (220) is attached to proximal section 210 by some of the omega-shaped connector members 250 seen in FIGS. 18 and 19. Omega-shaped connectors 250, it should be realized, are of different shape than struts 211, 221; these omega-shaped connectors 250 are formed to maximize flexibility, and it is to be understood that these struts need not be limited to the design disclosed here. It is envisioned that other flexible connections are possible.

The second distal section (230) having as its axis L" is positioned at the side of the first distal section 220, and has the advantage of being parallel to the latter prior to use. The second distal section 230 is intended to be inserted into a second distal blood vessel branching off from the bifurcation.

The two distal sections 220 and 230 have their proximal ends linked by the connection member 260, which is a weld joint comprising elements 261, 262 seen in FIG. 18. Dowel 261 fits into hole 262 to form weld 260.

Each of section 210, 220, and 230 is preferably formed from a tubular component perforated with a slotted tubular pattern such that the structure of sections 210, 220, 230 allows them to expand along their circumferences.

In practice section 210, 220, and 230 of stent is 200 can be manufactured from extruded cylindrical parts made of a bendable metal alloy such as 316 L stainless steel, but may also be made from other known metals such as nitinol. The external diameter of sections 210, 220, 230 typically ranges from 1 mm to 4 mm prior to use, and can be expanded further than 2 mm and 8 mm.

Sections 210, 220 are preferably manufactured from a single tubular part in which flexible connectors, such as omega-shaped connectors 250 are formed via machining.

Weld points 261, 262 are preferably joined by means of, for example, laser welding, or other acceptable alternatives.

Figure 20:
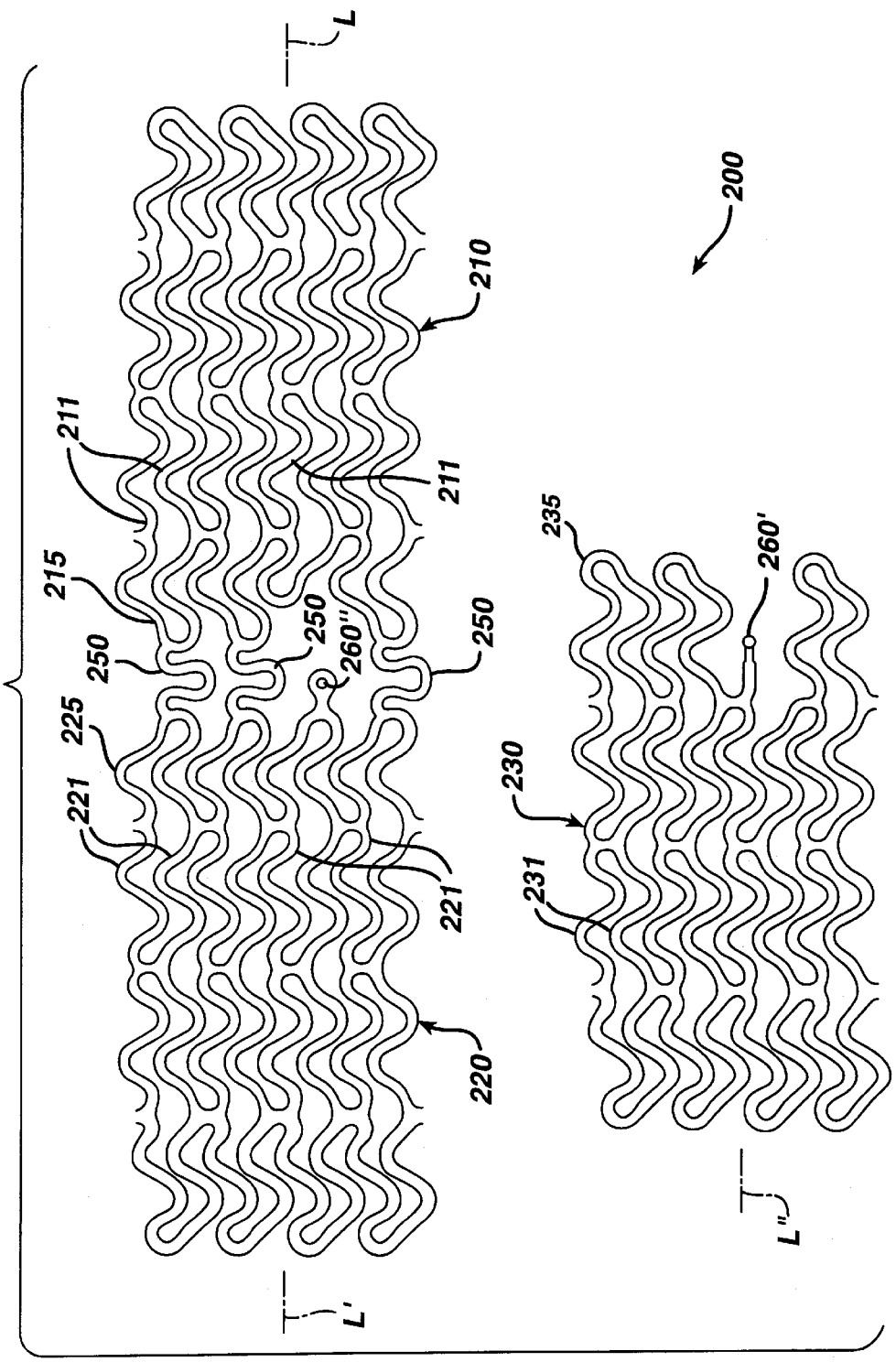
FIGS. 20 and 21 are perspective views of the stent of FIGS. 18 and 19 with an alternate type of connector joint.
Figure 21:
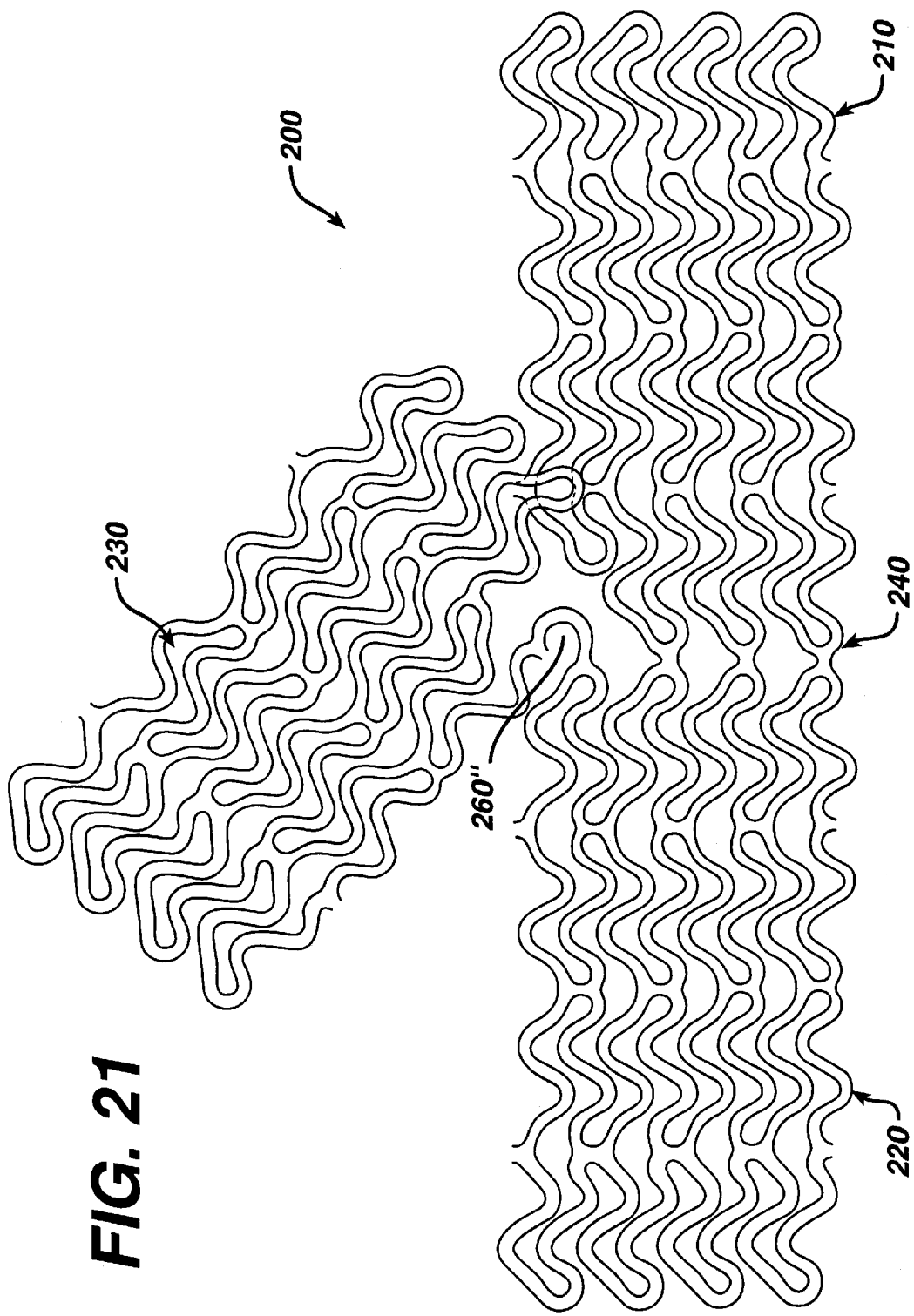

For instance, it is easily envisioned to use a ball and socket joint to connect the first and second tubular sections. The ball portion 260' of the joint can be placed on a strut in one of the sections and the socket portion 260" of the joint can be placed on a strut in the other section. This can best be seen in FIGS. 20 and 21.

Furthermore, proximal end 235 of the second distal section 230 may be tapered at the other side of the connector 250. It extends forward in its peripheral area opposite the omega-shaped connectors 250. This tapered portion may also be determined by a plane that is inclined with reference to L' perpendicular to the plane of symmetry of the stent 200.

After expansion, when the stent 200 is installed at the a bifurcation of the two vessels, distal portion 215 of the proximal section 210 is fit together with the proximal ends 225, 235, of sections 220, 230 of the stent, and ensures maximum coverage of the dilated bifurcation area. This is especially true since weld 260 holds the relative position of sections 220, 230 and the relative positions of sections 210, 220 is set, and covered by omega-shaped connectors 250.

In this way, once in place, the whole of the grid of the bifurcated stent 200 covers the proximal and distal portions of the two branching vessels and the whole of the dilated bifurcation area.

The stents themselves can be made from any high density material or composite. These stents can be balloon expandable or self-expanding or a combination of both. They can be used on catheters as described herein or on standard catheters.

These and other objects of the present invention are accomplished in a stent delivery system which consists of an ingeniously modified angioplasty catheter. Typical angioplasty catheters contain a central lumen useful for stringing a guidewire therethrough. The guidewire then guides the balloon from a point outside the body, along its length, to a point which is about to be stented. The balloon of the angioplasty catheter holds the stent as it is guided through the vasculature. When the obstruction is reached, the balloon is inflated, the stent is similarly inflated, and then the balloon can be deflated. Upon deflation, the balloon can be retracted through the vasculature along the guidewire.

In the present invention, a second guidewire lumen is placed at least within the balloon. (It should also be realized that the second guidewire lumen also can readily be placed along a length of the catheter shaft.) This second guidewire lumen is useful for attacking the bifurcated vessel. What occurs, therefore, is the following: a large stent is placed on the balloon so modified. Thereafter, the guidewire is tracked through the body to a point past the obstruction, which for the purposes described herein, is presumed to occur at or near a bifurcation. Onto the guidewire is tracked the modified stent delivery system. The balloon guidewire lumen is placed on to the guidewire outside the body and it is then moved along the guidewire to a point inside the body. The exit portion of the second balloon guidewire lumen is somewhere proximal to the distal end of the balloon, so that the entire balloon can be moved to a position along the vasculature at the obstruction in the body passageway.

When the obstruction is reached, the balloon can be inflated. This will usually take care of the "base" and one of the "legs" of the bifurcation. When inflated, a stent which is associated with the stent delivery system is similarly inflated. This stent has an opening situated along a portion of its wall. This opening is useful for opening the second leg of the bifurcated area.

The second area is opened in the following manner: a second balloon angioplasty catheter, this time containing a single basic stent is placed along the guidewire during positioning of the balloon catheter. A second guidewire is then strung through the catheter to a position where it emerges from the second opening. Then, the second catheter is guided along the second guidewire so that it, too, is placed along the second guidewire after the guidewire emerges from the distal opening of the balloon second guidewire opening. Then, the second catheter can be inflated when it is resident in the second "leg" of the bifurcation. At that point, because the first leg has already been expanded and the base of the bifurcation has been expanded, once the second leg of the bifurcation is expanded, the entire bifurcation has been attended to and the patient is properly stented.

Further, there is disclosed a method of stent placement which comprises first guiding a guidewire through the vasculature. Second, a balloon catheter which contains two guidewire lumens is strung along the guidewire into position at the bifurcation. The distal opening of the second guidewire lumen abuts the proximal end of the bifurcation. Thereafter, a second guidewire is strung through the first balloon catheter and out the distal opening of the second guidewire lumen. Thus, resident in the second bifurcation leg is the second guidewire. Then, a second standard stent delivery balloon catheter is guided along the second guidewire to a position within the bifurcation. Typically, expansion of both stents can be done one right after the other after proper placement of the first and second balloons.

What is claimed is:

1. A bifurcated stent comprising:

a proximal tubular section;

a first distal tubular section, said first distal tubular section connected to said proximal section by connector members; and a second distal tubular section, said first and second distal tubular sections welded together at their proximal ends; and wherein the weld is a spot weld formed between a dowel and a hole each placed respectively on one of said distal tubular sections.

2. The stent of claim 1 wherein said distal tubular sections and said proximal tubular section are expandable to different diameters.

3. A bifurcated stent comprising:

a proximal tubular section;

a first distal tubular section, said first distal tubular section connected to said proximal section by connector members; and a second distal tubular section, said first and second distal tubular sections welded together at their proximal ends;

wherein the connector members are omega-shaped; and wherein the connector members are continuously placed around the circumference of the first distal section.

4. The stent of claim 3 wherein the strut shape of the connector members are different than the strut shape of the struts in the proximal and distal sections.

5. The stent of claim 3 wherein said distal end and proximal sections are expandable to different diameters.

6. A bifurcated stent comprising:

a proximal tubular section;

a first distal tubular section, said first distal tubular section connected to said proximal section by connector members; and a second distal tubular section, said first and second distal tubular sections attached together at their proximal ends by a ball and socket joint wherein the ball is part of a strut of one of said distal sections and the socket is part of a strut of the other of said distal sections.

* * * * *